(12) United States Patent
Jones

(10) Patent No.: US 6,504,009 B1
(45) Date of Patent: Jan. 7, 2003

(54) TRANSCRIPTIONAL REGULATOR

(75) Inventor: Michael H. Jones, Ibaraki (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/418,780

(22) Filed: Oct. 15, 1999

Related U.S. Application Data

(63) Continuation-in-part of application No. PCT/JP98/01782, filed on Apr. 17, 1998.

(30) Foreign Application Priority Data

Apr. 18, 1997 (JP) .............................................. 9/116402

(51) Int. Cl.[7] .............................................. C07K 14/00
(52) U.S. Cl. ...................................................... 530/350
(58) Field of Search .......................................... 530/350

(56) References Cited

PUBLICATIONS

Beck et al., "A homologue of the Drosphila female sterile homeotic (fsh) gene in the class II region of the human MHC," DNA Sequence, vol. 2, pp. 203–210, 1992.
Denis et al., "A novel, mitogen–activated nuclear kinase is related to a Drosophila developmental regulator," Genes & Development, vol. 10, pp. 261–271, 1996.
Haynes et al., "The *Drosphila fsh* Locus, a Maternal Effect Homeotic Gene, Encodes Apparent Membrane Proteins[1]," Developmental Biology, vol. 134, pp. 246–257, 1989.
Jones et al., "Identification and Characterization of BRDT: A Testis–Specific Gene Related to the Bromodoma in Genes RING3 and *Drosophila fsh*," vol. 45, pp. 529–534, 1997.
Nomura et al., "Prediction of the Coding Sequences of Unidentified Human Genes. II. The Coding Sequences of 40 New Genes . . . ," DNA Research, vol. 1, pp. 223–229, 1994.
Haynes et al., "The bromodomain: a conserved sequence . . . ", 1992, Nucleic Acid Research, 20(10);2603.
Jones et al., "Identification and Characterization of BPTF, a Novel . . . ", 2000, Genomics, 63(1);35–39.
Nicolas et al., "Molecular cloning of polybromo, a nuclear protein . . .", 1996, Gene, 175(1–2);233–240.
GenBank Accession No. H64204, Oct. 14, 1995.

*Primary Examiner*—Karen Cochrane Carlson
(74) *Attorney, Agent, or Firm*—Fish & Richardson PC

(57) ABSTRACT

A database search using the sequence of transcriptional regulator "RING3" having a bromodomain identified an EST sequence that is highly homologous with RING3. Using primers prepared based on the EST sequence, a gene encoding a novel transcriptional regulator having a bromodomain has been successfully isolated from a human testis cDNA library by polymerase chain reactions. The results of analysis of the isolated gene revealed that this gene is expressed strongly in testis cells with a potent proliferative ability. The use of the above transcriptional regulator and its gene enables screening candidate compounds for factors interacting with the transcriptional regulator or drugs controlling the activity of the regulator.

51 Claims, 4 Drawing Sheets

```
            VIA                  VIB              IX
            34                   66               108
TSB         CSEILKEMLAKKHFS      YYTIIKNPMDL      YNKPGDDIVLMAQALE
RING3       YLHKVVMKALWKHQF      YHKIIKQPMOM      YNKPTDDIVLMAQTLE
fsh         YILKTVMKVIWKHHF      YHKIIKQPMOM      YNKPGEDVVVMAQTLE VIA (2)              VIB (2)          VIII
            276                  309              331
TSB         CSEILKEMLAKKHFS      YDVVKNRMDL       YKDAYSF
RING3       CNGILKELLSKKHAA      YHDIKHPMDL       YRDAQEF
fsh         CNEILKELFSKKHSG      YHDIKHPMDL       YQSAPEF IX (2)               III
            351                  511
TSB         YNPPDHEVVTYARMLQD    NYDEKRQL
RING3       YNPPDHDVVAYARKLQD    SYDEKRQL
fsh         YNPPDHDVVAYGRKLQD    SYDEKRQL
```

Fig. 4
A
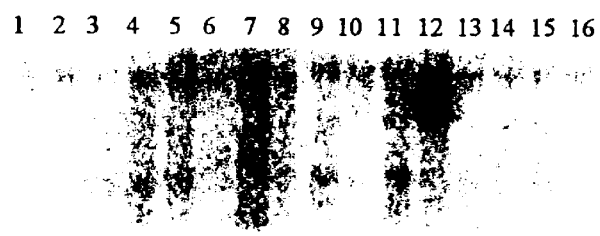
B
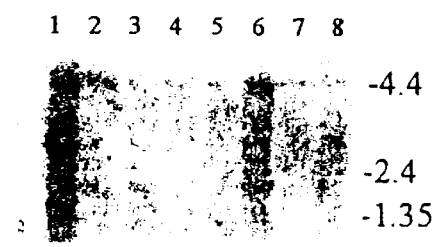

SEQUENCE LISTING

<160> NUMBER OF SEQ ID NOS: 28

<210> SEQ ID NO 1
<211> LENGTH: 947
<212> TYPE: PRT
<213> ORGANISM: Homo sapiens

<400> SEQUENCE: 1

Met Ser Leu Pro Ser Arg Gln Thr Ala Ile Ile Val Asn Pro Pro Pro

-continued

```
  1               5                    10                   15
Pro Glu Tyr Ile Asn Thr Lys Lys Asn Gly Arg Leu Thr Asn Gln Leu
                 20                  25                  30
Gln Tyr Leu Gln Lys Val Val Leu Lys Asp Leu Trp Lys His Ser Phe
             35                  40                  45
Ser Trp Pro Phe Gln Arg Pro Val Asp Ala Val Lys Leu Lys Leu Pro
     50                  55                  60
Asp Tyr Tyr Thr Ile Ile Lys Asn Pro Met Asp Leu Asn Thr Ile Lys
 65                  70                  75                  80
Lys Arg Leu Glu Asn Lys Tyr Tyr Ala Lys Ala Ser Glu Cys Ile Glu
                 85                  90                  95
Asp Phe Asn Thr Met Phe Ser Asn Cys Tyr Leu Tyr Asn Lys Pro Gly
                100                 105                 110
Asp Asp Ile Val Leu Met Ala Gln Ala Leu Glu Lys Leu Phe Met Gln
            115                 120                 125
Lys Leu Ser Gln Met Pro Gln Glu Glu Gln Val Val Gly Val Lys Glu
        130                 135                 140
Arg Ile Lys Lys Gly Thr Gln Gln Asn Ile Ala Val Ser Ser Ala Lys
145                 150                 155                 160
Glu Lys Ser Ser Pro Ser Ala Thr Glu Lys Val Phe Lys Gln Gln Glu
                165                 170                 175
Ile Pro Ser Val Phe Pro Lys Thr Ser Ile Ser Pro Leu Asn Val Val
            180                 185                 190
Gln Gly Ala Ser Val Asn Ser Ser Gln Thr Ala Ala Gln Val Thr
        195                 200                 205
Lys Gly Val Lys Arg Lys Ala Asp Thr Thr Thr Pro Ala Thr Ser Ala
    210                 215                 220
Val Lys Ala Ser Ser Glu Phe Ser Pro Thr Phe Thr Glu Lys Ser Val
225                 230                 235                 240
Ala Leu Pro Pro Ile Lys Glu Asn Met Pro Lys Asn Val Leu Pro Asp
                245                 250                 255
Ser Gln Gln Gln Tyr Asn Val Val Glu Thr Val Lys Val Thr Glu Gln
                260                 265                 270
Leu Arg His Cys Ser Glu Ile Leu Lys Glu Met Leu Ala Lys Lys His
            275                 280                 285
Phe Ser Tyr Ala Trp Pro Phe Tyr Asn Pro Val Asp Val Asn Ala Leu
    290                 295                 300
Gly Leu His Asn Tyr Tyr Asp Val Val Lys Asn Pro Met Asp Leu Gly
305                 310                 315                 320
Thr Ile Lys Glu Lys Met Asp Asn Gln Glu Tyr Lys Asp Ala Tyr Ser
                325                 330                 335
Phe Ala Ala Asp Val Arg Leu Met Phe Met Asn Cys Tyr Lys Tyr Asn
            340                 345                 350
Pro Pro Asp His Glu Val Val Thr Met Ala Arg Met Leu Gln Asp Val
        355                 360                 365
Phe Glu Thr His Phe Ser Lys Ile Pro Ile Glu Pro Val Glu Ser Met
    370                 375                 380
Pro Leu Cys Tyr Ile Lys Thr Asp Ile Thr Glu Thr Thr Gly Arg Glu
385                 390                 395                 400
Asn Thr Asn Glu Ala Ser Ser Glu Gly Asn Ser Ser Asp Asp Ser Glu
                405                 410                 415
Asp Glu Arg Val Lys Arg Leu Ala Lys Leu Gln Glu Gln Leu Lys Ala
            420                 425                 430
```

```
Val His Gln Gln Leu Gln Val Leu Ser Gln Val Pro Phe Arg Lys Leu
        435                 440                 445
Asn Lys Lys Lys Glu Lys Ser Lys Lys Glu Lys Lys Lys Glu Lys Val
450                 455                 460
Asn Asn Ser Asn Glu Asn Pro Arg Lys Met Cys Glu Gln Met Arg Leu
465                 470                 475                 480
Lys Glu Lys Ser Lys Arg Asn Gln Pro Lys Lys Arg Lys Gln Gln Phe
                485                 490                 495
Ile Gly Leu Lys Ser Glu Asp Glu Asp Asn Ala Lys Pro Met Asn Tyr
                500                 505                 510
Asp Glu Lys Arg Gln Leu Ser Leu Asn Ile Asn Lys Leu Pro Gly Asp
                515                 520                 525
Lys Leu Gly Arg Val Val His Ile Ile Gln Ser Arg Glu Pro Ser Leu
                530                 535                 540
Ser Asn Ser Asn Pro Asp Glu Ile Glu Ile Asp Phe Glu Thr Leu Lys
545                 550                 555                 560
Ala Ser Thr Leu Arg Glu Leu Glu Lys Tyr Val Ser Ala Cys Leu Arg
                565                 570                 575
Lys Arg Pro Leu Lys Pro Ala Lys Lys Ile Met Met Ser Lys Glu
                580                 585                 590
Glu Leu His Ser Gln Lys Lys Gln Glu Leu Glu Lys Arg Leu Leu Asp
                595                 600                 605
Val Asn Asn Gln Leu Asn Ser Arg Lys Arg Gln Thr Lys Ser Asp Lys
                610                 615                 620
Thr Gln Pro Ser Lys Ala Val Glu Asn Val Ser Arg Leu Ser Glu Ser
625                 630                 635                 640
Ser Ser Ser Ser Ser Ser Ser Glu Ser Glu Ser Ser Ser Asp
                645                 650                 655
Leu Ser Ser Ser Asp Ser Ser Asp Ser Glu Ser Glu Met Phe Pro Lys
                660                 665                 670
Phe Thr Glu Val Lys Pro Asn Asp Ser Pro Ser Lys Glu His Val Lys
                675                 680                 685
Lys Met Lys Asn Glu Cys Ile Leu Pro Glu Gly Arg Thr Gly Val Thr
                690                 695                 700
Gln Ile Gly Tyr Cys Val Gln Asp Thr Thr Ser Ala Asn Thr Thr Leu
705                 710                 715                 720
Val His Gln Thr Thr Pro Ser His Val Met Pro Pro Asn His His Gln
                725                 730                 735
Leu Ala Phe Asn Tyr Gln Glu Leu Glu His Leu Gln Thr Val Lys Asn
                740                 745                 750
Ile Ser Pro Leu Gln Ile Leu Pro Pro Ser Gly Asp Ser Glu Gln Leu
                755                 760                 765
Ser Asn Gly Ile Thr Val Met His Pro Ser Gly Asp Ser Asp Thr Thr
                770                 775                 780
Met Leu Glu Ser Glu Cys Gln Ala Pro Val Gln Lys Asp Ile Lys Ile
785                 790                 795                 800
Lys Asn Ala Asp Ser Trp Lys Ser Leu Gly Lys Pro Val Lys Pro Ser
                805                 810                 815
Gly Val Met Lys Ser Ser Asp Glu Leu Phe Asn Gln Phe Arg Lys Ala
                820                 825                 830
Ala Ile Glu Lys Glu Val Lys Ala Arg Thr Gln Glu Leu Ile Arg Lys
                835                 840                 845
```

```
His Leu Glu Gln Asn Thr Lys Glu Leu Lys Ala Ser Gln Glu Asn Gln
    850                 855                 860

Arg Asp Leu Gly Asn Gly Leu Thr Val Glu Ser Phe Ser Asn Lys Ile
865                 870                 875                 880

Gln Asn Lys Cys Ser Gly Glu Gln Lys Glu His Pro Gln Ser Ser
                885                 890                 895

Glu Ala Gln Asp Lys Ser Lys Leu Trp Leu Leu Lys Arg Asp Leu
                900                 905                 910

Ala Arg Pro Lys Glu Gln Glu Arg Arg Arg Glu Ala Met Val Gly
            915                 920                 925

Thr Ile Asp Met Thr Leu Gln Ser Asp Ile Met Thr Met Phe Glu Asn
        930                 935                 940

Asn Phe Asp
945

<210> SEQ ID NO 2
<211> LENGTH: 3104
<212> TYPE: DNA
<213> ORGANISM: Homo sapiens
<220> FEATURE:
<221> NAME/KEY: CDS
<222> LOCATION: (106)...(2946)

<400> SEQUENCE: 2
ggcaagatgt tcctgggagg tcaagttaag agtcaaaaat aattcattag atttaacaat      60
ttagcatgga catgtacttg tagacaggat tcaaagcagt taaga atg tct ctg cca    117
                                              Met Ser Leu Pro
                                                1 agt cga caa aca gct att att gtt aac cct cct cca cca gaa tat ata      165
Ser Arg Gln Thr Ala Ile Ile Val Asn Pro Pro Pro Pro Glu Tyr Ile
  5                  10                  15                  20 aat act aag aaa aat ggg cga ttg aca aat caa ctt cag tat cta caa      213
Asn Thr Lys Lys Asn Gly Arg Leu Thr Asn Gln Leu Gln Tyr Leu Gln
                 25                  30                  35 aaa gtt gtc cta aag gat tta tgg aag cat agt ttt tca tgg ccc ttt      261
Lys Val Val Leu Lys Asp Leu Trp Lys His Ser Phe Ser Trp Pro Phe
             40                  45                  50 caa cgt cct gtg gat gct gtg aaa cta aag ttg cct gat tat tat acc      309
Gln Arg Pro Val Asp Ala Val Lys Leu Lys Leu Pro Asp Tyr Tyr Thr
         55                  60                  65 att ata aaa aac cca atg gat tta aat aca att aag aag cgc ttg gag      357
Ile Ile Lys Asn Pro Met Asp Leu Asn Thr Ile Lys Lys Arg Leu Glu
     70                  75                  80 aat aaa tat tat gcg aag gct tca gaa tgt ata gaa gac ttc aat aca      405
Asn Lys Tyr Tyr Ala Lys Ala Ser Glu Cys Ile Glu Asp Phe Asn Thr
 85                  90                  95                 100 atg ttc tca aat tgt tat tta tat aac aag cct gga gat gac att gtt      453
Met Phe Ser Asn Cys Tyr Leu Tyr Asn Lys Pro Gly Asp Asp Ile Val
                105                 110                 115 ctt atg gca caa gct cta gag aag ctg ttt atg cag aaa tta tct cag      501
Leu Met Ala Gln Ala Leu Glu Lys Leu Phe Met Gln Lys Leu Ser Gln
            120                 125                 130 atg cca caa gaa gag caa gtt gtg ggt gtt aag gaa aga atc aag aaa      549
Met Pro Gln Glu Glu Gln Val Val Gly Val Lys Glu Arg Ile Lys Lys
        135                 140                 145 ggc act caa cag aat ata gct gtt tct tct gct aaa gaa aaa tca tca      597
Gly Thr Gln Gln Asn Ile Ala Val Ser Ser Ala Lys Glu Lys Ser Ser
    150                 155                 160 ccc agc gca aca gaa aaa gta ttt aag cag caa gaa att cct tct gta      645
```

```
                                                                -continued

Pro Ser Ala Thr Glu Lys Val Phe Lys Gln Gln Glu Ile Pro Ser Val
165                 170                 175                 180 ttt cct aag aca tct att tct ccc ttg aac gtg gta cag gga gct tca          693
Phe Pro Lys Thr Ser Ile Ser Pro Leu Asn Val Val Gln Gly Ala Ser
                    185                 190                 195 gtc aac tcc agt tca caa act gcg gcc caa gtt aca aaa ggt gtg aag          741
Val Asn Ser Ser Ser Gln Thr Ala Ala Gln Val Thr Lys Gly Val Lys
                200                 205                 210 agg aaa gca gat aca aca act cct gca act tca gca gtt aaa gca agt          789
Arg Lys Ala Asp Thr Thr Thr Pro Ala Thr Ser Ala Val Lys Ala Ser
            215                 220                 225 agt gaa ttt tct cca aca ttc aca gaa aaa tca gtg gca ctg cca cct          837
Ser Glu Phe Ser Pro Thr Phe Thr Glu Lys Ser Val Ala Leu Pro Pro
        230                 235                 240 ata aaa gaa aat atg cca aag aat gtt ttg cca gat tct cag caa caa          885
Ile Lys Glu Asn Met Pro Lys Asn Val Leu Pro Asp Ser Gln Gln Gln
245                 250                 255                 260 tat aat gtt gtg gag act gtt aaa gta act gaa caa tta agg cac tgt          933
Tyr Asn Val Val Glu Thr Val Lys Val Thr Glu Gln Leu Arg His Cys
                    265                 270                 275 agt gag att ctt aaa gaa atg ctt gca aag aaa cat ttt tca tat gca          981
Ser Glu Ile Leu Lys Glu Met Leu Ala Lys Lys His Phe Ser Tyr Ala
                280                 285                 290 tgg ccc ttt tat aat cct gtt gac gtt aat gct ttg gga ctc cat aac         1029
Trp Pro Phe Tyr Asn Pro Val Asp Val Asn Ala Leu Gly Leu His Asn
            295                 300                 305 tac tat gac gtt gtc aaa aat ccg atg gat ctt gga act att aag gag         1077
Tyr Tyr Asp Val Val Lys Asn Pro Met Asp Leu Gly Thr Ile Lys Glu
        310                 315                 320 aaa atg gat aac caa gaa tat aag gat gca tac tca ttt gcg gca gat         1125
Lys Met Asp Asn Gln Glu Tyr Lys Asp Ala Tyr Ser Phe Ala Ala Asp
325                 330                 335                 340 gtt aga tta atg ttc atg aat tgc tac aag tac aat cct cca gat cac         1173
Val Arg Leu Met Phe Met Asn Cys Tyr Lys Tyr Asn Pro Pro Asp His
                    345                 350                 355 gaa gtt gtg aca atg gca aga atg ctt cag gat gtt ttc gaa acg cat         1221
Glu Val Val Thr Met Ala Arg Met Leu Gln Asp Val Phe Glu Thr His
                360                 365                 370 ttt tca aag atc ccg att gaa cct gtt gag agt atg cct tta tgt tac         1269
Phe Ser Lys Ile Pro Ile Glu Pro Val Glu Ser Met Pro Leu Cys Tyr
        375                 380                 385 atc aaa aca gat atc aca gaa acc act ggt aga gag aac act aat gaa         1317
Ile Lys Thr Asp Ile Thr Glu Thr Thr Gly Arg Glu Asn Thr Asn Glu
390                 395                 400 gcc tcc tct gaa ggg aac tct tct gat gat tct gaa gat gag cga gtt         1365
Ala Ser Ser Glu Gly Asn Ser Ser Asp Asp Ser Glu Asp Glu Arg Val
                    410                 415                 420 aag cgt ctt gca aag ctt cag gag cag ctt aaa gct gta cat caa cag         1413
Lys Arg Leu Ala Lys Leu Gln Glu Gln Leu Lys Ala Val His Gln Gln
                425                 430                 435 ctc cag gtt ttg tcc caa gta cct ttc cgt aag cta aat aaa aag aaa         1461
Leu Gln Val Leu Ser Gln Val Pro Phe Arg Lys Leu Asn Lys Lys Lys
        440                 445                 450 gag aag tct aaa aag gaa aag aaa aaa gaa aag gtt aat aac agc aat         1509
Glu Lys Ser Lys Lys Glu Lys Lys Lys Glu Lys Val Asn Asn Ser Asn
455                 460                 465 gaa aat cca aga aaa atg tgt gag caa atg agg cta aag gaa aag tcc         1557
Glu Asn Pro Arg Lys Met Cys Glu Gln Met Arg Leu Lys Glu Lys Ser
            470                 475                 480
```

-continued

| | |
|---|---|
| aag aga aat cag cca aag aaa agg aaa caa cag ttc att ggt cta aaa<br>Lys Arg Asn Gln Pro Lys Lys Arg Lys Gln Gln Phe Ile Gly Leu Lys<br>485                      490                      495                      500 | 1605 |
| tct gaa gat gaa gat aat gct aaa cct atg aac tat gat gag aaa agg<br>Ser Glu Asp Glu Asp Asn Ala Lys Pro Met Asn Tyr Asp Glu Lys Arg<br>                505                      510                      515 | 1653 |
| cag tta agt ctg aat ata aac aaa ctc cct gga gat aaa ctt ggg cga<br>Gln Leu Ser Leu Asn Ile Asn Lys Leu Pro Gly Asp Lys Leu Gly Arg<br>            520                      525                      530 | 1701 |
| gta gtt cac ata ata caa tca aga gag cct tct ctg agc aat tcc aat<br>Val Val His Ile Ile Gln Ser Arg Glu Pro Ser Leu Ser Asn Ser Asn<br>                535                      540                      545 | 1749 |
| cct gat gag ata gag ata gac ttt gaa aca ctg aaa gca tca aca cta<br>Pro Asp Glu Ile Glu Ile Asp Phe Glu Thr Leu Lys Ala Ser Thr Leu<br>550                      555                      560 | 1797 |
| aga gaa tta gaa aaa tat gtt tcg gca tgt cta aga aag aga cca tta<br>Arg Glu Leu Glu Lys Tyr Val Ser Ala Cys Leu Arg Lys Arg Pro Leu<br>565                      570                      575                      580 | 1845 |
| aaa cct cct gct aag aaa ata atg atg tcc aaa gaa gaa ctt cac tca<br>Lys Pro Pro Ala Lys Lys Ile Met Met Ser Lys Glu Glu Leu His Ser<br>                585                      590                      595 | 1893 |
| cag aaa aaa cag gaa ttg gaa aag cgg tta ctg gat gtt aat aat cag<br>Gln Lys Lys Gln Glu Leu Glu Lys Arg Leu Leu Asp Val Asn Asn Gln<br>            600                      605                      610 | 1941 |
| tta aat tct aga aaa cgt caa aca aaa tct gat aaa acg caa cca tcc<br>Leu Asn Ser Arg Lys Arg Gln Thr Lys Ser Asp Lys Thr Gln Pro Ser<br>                615                      620                      625 | 1989 |
| aaa gct gtt gaa aat gtt tcc cga ctg agt gag agc agc agc agc agc<br>Lys Ala Val Glu Asn Val Ser Arg Leu Ser Glu Ser Ser Ser Ser Ser<br>630                      635                      640 | 2037 |
| agc agc tca tca gag tct gaa agt agc agc agt gac tta agc tct tca<br>Ser Ser Ser Ser Glu Ser Glu Ser Ser Ser Ser Asp Leu Ser Ser Ser<br>645                      650                      655                      660 | 2085 |
| gac agc agt gat tct gaa tca gaa atg ttc cct aag ttt aca gaa gta<br>Asp Ser Ser Asp Ser Glu Ser Glu Met Phe Pro Lys Phe Thr Glu Val<br>                      665                      670                      675 | 2133 |
| aaa cca aat gat tct cct tct aaa gag cat gta aag aaa atg aag aat<br>Lys Pro Asn Asp Ser Pro Ser Lys Glu His Val Lys Lys Met Lys Asn<br>            680                      685                      690 | 2181 |
| gaa tgc ata ctg cct gaa gga aga aca ggc gtc aca cag ata gga tat<br>Glu Cys Ile Leu Pro Glu Gly Arg Thr Gly Val Thr Gln Ile Gly Tyr<br>                695                      700                      705 | 2229 |
| tgt gtg caa gac aca acc tct gcc aat act acc ctt gtt cat cag acc<br>Cys Val Gln Asp Thr Thr Ser Ala Asn Thr Thr Leu Val His Gln Thr<br>710                      715                      720 | 2277 |
| aca cct tca cat gta atg cca cca aat cac cac caa tta gca ttt aat<br>Thr Pro Ser His Val Met Pro Pro Asn His His Gln Leu Ala Phe Asn<br>725                      730                      735                      740 | 2325 |
| tat caa gaa tta gaa cat tta cag act gtg aaa aac att tca cct tta<br>Tyr Gln Glu Leu Glu His Leu Gln Thr Val Lys Asn Ile Ser Pro Leu<br>                745                      750                      755 | 2373 |
| caa att ctg cct ccc tca ggt gat tct gaa cag ctc tca aat ggc ata<br>Gln Ile Leu Pro Pro Ser Gly Asp Ser Glu Gln Leu Ser Asn Gly Ile<br>            760                      765                      770 | 2421 |
| act gtg atg cat cca tct ggt gat agt gac aca acg atg tta gaa tct<br>Thr Val Met His Pro Ser Gly Asp Ser Asp Thr Thr Met Leu Glu Ser<br>                775                      780                      785 | 2469 |
| gaa tgt caa gct cct gta cag aag gat ata aag att aag aat gca gat<br>Glu Cys Gln Ala Pro Val Gln Lys Asp Ile Lys Ile Lys Asn Ala Asp<br>    790                      795                      800 | 2517 |

-continued

```
tca tgg aaa agt tta ggc aaa cca gtg aaa cca tca ggt gta atg aaa      2565
Ser Trp Lys Ser Leu Gly Lys Pro Val Lys Pro Ser Gly Val Met Lys
805                 810                 815                 820 tcc tca gat gag ctc ttc aac caa ttt aga aaa gca gcc ata gaa aag      2613
Ser Ser Asp Glu Leu Phe Asn Gln Phe Arg Lys Ala Ala Ile Glu Lys
                825                 830                 835 gaa gta aaa gct cgg aca cag gaa ctc ata cgg aag cat ttg gaa caa      2661
Glu Val Lys Ala Arg Thr Gln Glu Leu Ile Arg Lys His Leu Glu Gln
            840                 845                 850 aat aca aag gaa cta aaa gca tct caa gaa aat cag agg gat ctt ggg      2709
Asn Thr Lys Glu Leu Lys Ala Ser Gln Glu Asn Gln Arg Asp Leu Gly
        855                 860                 865 aat gga ttg act gta gaa tct ttt tca aat aaa ata caa aac aag tgc      2757
Asn Gly Leu Thr Val Glu Ser Phe Ser Asn Lys Ile Gln Asn Lys Cys
    870                 875                 880 tct gga gaa gag cag aaa gaa cat ccg cag tca tca gaa gct caa gat      2805
Ser Gly Glu Glu Gln Lys Glu His Pro Gln Ser Ser Glu Ala Gln Asp
885                 890                 895                 900 aaa tcc aaa ctc tgg ctt ctc aaa gac cgt gat tta gcc agg ccg aaa      2853
Lys Ser Lys Leu Trp Leu Leu Lys Asp Arg Asp Leu Ala Arg Pro Lys
                905                 910                 915 gaa caa gag agg agg agg aga gaa gcc atg gtg ggt acc att gat atg      2901
Glu Gln Glu Arg Arg Arg Arg Glu Ala Met Val Gly Thr Ile Asp Met
            920                 925                 930 acc ctt caa agt gac att atg aca atg ttt gaa aac aac ttt gat          2946
Thr Leu Gln Ser Asp Ile Met Thr Met Phe Glu Asn Asn Phe Asp
        935                 940                 945 taaaactcag tttttaaatt aaccatccac ttaaaatgaa tggtaaaaga tcaaaatgca    3006
tatggtaaaa tgattgcttt cagataacaa gataccaatc ttatattgta ttttgactgc    3066
tctaaaatga ttaaacagtt ttcacttaca aaaaaaa                             3104
```

<210> SEQ ID NO 3
<211> LENGTH: 22
<212> TYPE: DNA
<213> ORGANISM: Artificial Sequence
<220> FEATURE:
<223> OTHER INFORMATION: synthetically generated primer

<400> SEQUENCE: 3
aatgtctctg ccaagtcgac aa                                             22

<210> SEQ ID NO 4
<211> LENGTH: 22
<212> TYPE: DNA
<213> ORGANISM: Artificial Sequence
<220> FEATURE:
<223> OTHER INFORMATION: synthetically generated primer

<400> SEQUENCE: 4
agcatccaca ggacgttgaa ag                                             22

<210> SEQ ID NO 5
<211> LENGTH: 15
<212> TYPE: PRT
<213> ORGANISM: Homo sapiens

<400> SEQUENCE: 5

Cys Ser Glu Ile Leu Lys Glu Met Leu Ala Lys Lys His Phe Ser
1               5                   10                  15

```
<210> SEQ ID NO 6
<211> LENGTH: 11
<212> TYPE: PRT
<213> ORGANISM: Homo sapiens

<400> SEQUENCE: 6

Tyr Tyr Thr Ile Ile Lys Asn Pro Met Asp Leu
1               5                   10

<210> SEQ ID NO 7
<211> LENGTH: 16
<212> TYPE: PRT
<213> ORGANISM: Homo sapiens

<400> SEQUENCE: 7

Tyr Asn Lys Pro Gly Asp Asp Ile Val Leu Met Ala Gln Ala Leu Glu
1               5                   10                  15

<210> SEQ ID NO 8
<211> LENGTH: 15
<212> TYPE: PRT
<213> ORGANISM: Homo sapiens

<400> SEQUENCE: 8

Cys Ser Glu Ile Leu Lys Glu Met Leu Ala Lys Lys His Phe Ser
1               5                   10                  15

<210> SEQ ID NO 9
<211> LENGTH: 10
<212> TYPE: PRT
<213> ORGANISM: Homo sapiens

<400> SEQUENCE: 9

Tyr Asp Val Val Lys Asn Arg Met Asp Leu
1               5                   10

<210> SEQ ID NO 10
<211> LENGTH: 7
<212> TYPE: PRT
<213> ORGANISM: Homo sapiens

<400> SEQUENCE: 10

Tyr Lys Asp Ala Tyr Ser Phe
1               5

<210> SEQ ID NO 11
<211> LENGTH: 17
<212> TYPE: PRT
<213> ORGANISM: Homo sapiens

<400> SEQUENCE: 11

Tyr Asn Pro Pro Asp His Glu Val Val Thr Met Ala Arg Met Leu Gln
1               5                   10                  15

Asp

<210> SEQ ID NO 12
<211> LENGTH: 8
<212> TYPE: PRT
<213> ORGANISM: Homo sapiens

<400> SEQUENCE: 12

Asn Tyr Asp Glu Lys Arg Gln Leu
1               5
```

```
<210> SEQ ID NO 13
<211> LENGTH: 15
<212> TYPE: PRT
<213> ORGANISM: Homo sapiens

<400> SEQUENCE: 13

Tyr Leu His Lys Val Val Met Lys Ala Leu Trp Lys His Gln Phe
 1               5                  10                  15

<210> SEQ ID NO 14
<211> LENGTH: 11
<212> TYPE: PRT
<213> ORGANISM: Homo sapiens

<400> SEQUENCE: 14

Tyr His Lys Ile Ile Lys Gln Pro Met Asp Met
 1               5                  10

<210> SEQ ID NO 15
<211> LENGTH: 16
<212> TYPE: PRT
<213> ORGANISM: Homo sapiens

<400> SEQUENCE: 15

Tyr Asn Lys Pro Thr Asp Asp Ile Val Leu Met Ala Gln Thr Leu Glu
 1               5                  10                  15

<210> SEQ ID NO 16
<211> LENGTH: 15
<212> TYPE: PRT
<213> ORGANISM: Homo sapiens

<400> SEQUENCE: 16

Cys Asn Gly Ile Leu Lys Glu Leu Leu Ser Lys Lys His Ala Ala
 1               5                  10                  15

<210> SEQ ID NO 17
<211> LENGTH: 10
<212> TYPE: PRT
<213> ORGANISM: Homo sapiens

<400> SEQUENCE: 17

Tyr His Asp Ile Lys His Pro Met Asp Leu
 1               5                  10

<210> SEQ ID NO 18
<211> LENGTH: 7
<212> TYPE: PRT
<213> ORGANISM: Homo sapiens

<400> SEQUENCE: 18

Tyr Arg Asp Ala Gln Glu Phe
 1               5

<210> SEQ ID NO 19
<211> LENGTH: 17
<212> TYPE: PRT
<213> ORGANISM: Homo sapiens

<400> SEQUENCE: 19

Tyr Asn Pro Pro Asp His Asp Val Val Ala Met Ala Arg Lys Leu Gln
 1               5                  10                  15
Asp
```

```
<210> SEQ ID NO 20
<211> LENGTH: 8
<212> TYPE: PRT
<213> ORGANISM: Homo sapiens

<400> SEQUENCE: 20

Ser Tyr Asp Glu Lys Arg Gln Leu
 1               5

<210> SEQ ID NO 21
<211> LENGTH: 15
<212> TYPE: PRT
<213> ORGANISM: Drosophila melanogaster

<400> SEQUENCE: 21

Tyr Ile Leu Lys Thr Val Met Lys Val Ile Trp Lys His His Phe
 1               5                  10                  15

<210> SEQ ID NO 22
<211> LENGTH: 11
<212> TYPE: PRT
<213> ORGANISM: Drosophila melanogaster

<400> SEQUENCE: 22

Tyr His Lys Ile Ile Lys Gln Pro Met Asp Met
 1               5                  10

<210> SEQ ID NO 23
<211> LENGTH: 16
<212> TYPE: PRT
<213> ORGANISM: Drosophila melanogaster

<400> SEQUENCE: 23

Tyr Asn Lys Pro Gly Glu Asp Val Val Val Met Ala Gln Thr Leu Glu
 1               5                  10                  15

<210> SEQ ID NO 24
<211> LENGTH: 15
<212> TYPE: PRT
<213> ORGANISM: Drosophila melanogaster

<400> SEQUENCE: 24

Cys Asn Glu Ile Leu Lys Glu Leu Phe Ser Lys Lys His Ser Gly
 1               5                  10                  15

<210> SEQ ID NO 25
<211> LENGTH: 10
<212> TYPE: PRT
<213> ORGANISM: Drosophila melanogaster

<400> SEQUENCE: 25

Tyr His Asp Ile Lys His Pro Met Asp Leu
 1               5                  10

<210> SEQ ID NO 26
<211> LENGTH: 7
<212> TYPE: PRT
<213> ORGANISM: Drosophila melanogaster

<400> SEQUENCE: 26

Tyr Gln Ser Ala Pro Glu Phe
 1               5

<210> SEQ ID NO 27
<211> LENGTH: 17
```

-continued

```
<212> TYPE: PRT
<213> ORGANISM: Drosophila melanogaster

<400> SEQUENCE: 27

Tyr Asn Pro Pro Asp His Asp Val Val Ala Met Gly Arg Lys Leu Gln
1               5                   10                  15

Asp

<210> SEQ ID NO 28
<211> LENGTH: 8
<212> TYPE: PRT
<213> ORGANISM: Drosophila melanogaster

<400> SEQUENCE: 28

Ser Tyr Asp Glu Lys Arg Gln Leu
1               5
```

TRANSCRIPTIONAL REGULATOR

This application is a continuation-in-part of PCT/JP98/01782, filed Apr. 17, 1998, and claims priority from Japanese Application No. 9/116402, filed Apr. 18, 1997.

TECHNICAL FIELD

The present invention relates to a novel transcriptional regulator containing a bromodomain and a gene encoding it.

BACKGROUND ART

The bromodomain is a characteristic motif of amino acids found in transcriptional regulators, and is believed to be involved in interaction with other proteins, such as other transcriptional regulators. Proteins having a bromodomain usually contain one or two (Tamkun, J. W. et al., (1992) Cell, 68:561–572, Haynes, S. R. et al., (1992) Nuc. Acids Res., 20:2603), but sometimes as many as five bromodomain motifs (Nicolas, R. H. and Goodwin, G. H. (1996), Gene, 175(12):233–240). This motif is found in a wide variety of animals. For example, it is identified in yeast (Winston, F. et al., (1987), Genetics, 115:649–656; Laurent, B. C. et al., (1991), Proc. Natl. Acad. Sci. USA, 25 88:2687–2691), Drosophila (Digan, M. E. et al., (1986), Dev. Biol., 114:161–169; Tamkun, J. W. et al., (1992), Cell, 68:561–572), and mammals (Denis, G. V. and Green, M. R. (1996), Genes and Devel., 10:261–271; Yang, X. J. et al., (1996), Nature, 382:319–324).

All transcriptional regulators containing a bromodomain serve to control signal-dependent transcription in actively proliferating cells (Tamkun, J. W. et al., (1992), Cell, 68:561–572; Haynes, S. R. et al., (1992), Nuc. Acids Res., 20:2603). Due to this feature, it is suggested that cancer may develop if the gene for the protein containing a bromodomain is not normally controlled. In fact, several studies have shown that human transcriptional regulators with a bromodomain RING3, p300/CBP, and PCAF may be involved in oncogenesis.

RING3 was identified during an extensive analysis of the sequences of human class II major histocompatibility systems (Beck et al., (1992) DNA Seq. 2:203–210). The protein encoded by RING3 is homologous to D26362, a human gene (Nomura et al., (1994) DNA Res. 1:223–229) and fsh, a drosophila gene (Digan et al., (1986), Dev. Biol., 114: 161–169). All three genes encode proteins contain two copies of a bromodomain and a PEST sequences. The bromodomain is a motif consisting of 59 to 63 amino acid residues and is considered to be involved in protein-protein interactions. It is found among the transcriptional regulator proteins (Tamkun, J. W. et al., (1992) Cell, 68:561–572; Haynes, S. R. et al., (1992) Nuc. Acids Res. 20:2603). The PEST sequence is a cluster of proline (P), glutamic acid (E), serine (S) and threonine (T), which characterizes the proteins that undergo rapid proteolysis in the cell.

The protein encoded by RING3 has a molecular weight of 90 kD and has serine-threonine activity (Denis and Green, (1996) Genes and Devel. 10:261–271). Comparison of the sequences of RING3 and fsh with those of kinase domains of known serine-threonine kinases revealed that the sub-domains of the kinase motif are conserved, though in no particular order (most of them are similar to the corresponding sub-domains of a proto-oncogene c-mos). Kinase activity of RING3 is stimulated by interleukin-1 (IL-1) and forskolin, but not by a certain category of cytokines (Denis and Green, (1996) Genes and Devel. 10:261–271). A close relationship between kinase activity and growth phase in chronic and acute lymphocytic leukemia suggests the role RING3 plays in the leukemogenesis regulatory pathway (Denis and Green, (1996) Genes and Devel. 10:261–271). The analysis of the drosophila fsh gene suggested the interaction with the trithorax transcriptional regulator, a possible target for the putative phosphorylative activity of fsh (Digan et al., (1986) Dev. Biol. 114:161–169; Mozer and Dawid, (1989) Proc. Natl. Acad. Sci. USA 86:3738–3742). The triathorax gene and its homologue ALL-1 have a C4HC3 zinc finger, a motif commonly found among the genes present at leukemia breakpoints(Aasland et al., (1995) Trends Biochem. Sci. 20:56–59; Saha et al., (1995) *Proc. Natl. Acad. Sci. USA* 92:9737–9741).

In addition to RING3, at least two other bromodomain proteins, p300/CBP and PCAF, are associated with oncogenesis. Although p300 protein and CBP protein are encoded by different genes, they are extremely closely related, and therefore, they are often called p300/CBP. Mutations in CBP are often found in familial and sporadic cancers. Mutations in CBP sometimes result in Rubinstein-Taybi syndrome, which causes patients to develop various malignant tumors (Petrij et al., (1995) Nature 376:348–51). Furthermore, CBP is fused with MOZ at t(8;6)(p11;p13) translocation (Borrow et al., (1996) Nature Genet. 14:33–41). This fusion protein possibly causes leukemogenesis by its aberrant acetyltransferase activity (Brownwell and Allis, (1996) Curr. Opin. Genet. Devel. 6:176–184). Mutation in p300 is found in sporadic colon and gastric cancers (Muraoka et al., (1996) Oncogene 12:1565–1569), and p300 has been suggested to be a gene for a tumor-suppressing factor located on chromosome 22q. Another fact that suggests the role of p300/CBP in cancer is that it interacts with the known oncogenes. For example, it is a co-activator of c-Myb (Dai, et al., (1996) Genes and Devel. 10:528–540) and c-Fos (Bannister and Kouzarides, (1996) Nature 384:641–643) transcriptional factors, to which the E1A protein of Adenovirus bind (Yang et al., (1996) Nature 382:319–324). The interaction between E1A and p300/CBP is inhibited by PCAF, a bromodomain protein.

Like p300/CBP, PCAF also has histone acetyltransferase activity. PCAF, when exogenously expressed, can reduce the proliferation associated with E1A in cultured cells (Yang et al., (1996) Nature 382:319–324). Therefore one of the first mechanisms of the activity of the E1A oncogene may be to inhibit the interaction between PCAF and p300.

Thus, it is thought that aberrant regulation of transcriptional regulators containing a bromodomain may be closely related to various diseases, for example, cancer. Transcriptional regulators containing a bromodomain have thus recently received much attention as novel targets for treating cancer.

DISCLOSURE OF THE INVENTION

An objective of the present invention is to provide a novel transcriptional regulator having a bromodomain and DNA encoding said transcriptional regulator. Another objective of the present invention is to provide a vector carrying said DNA, a transformant retaining said DNA, and a process for producing a recombinant protein by utilizing said transformant. A further objective of the present invention is to provide a method of screening a compound that binds to said transcriptional regulator.

To solve the problems described above, the inventors searched a database based on the sequence of RING3 transcriptional regulator with a bromodomain and found several EST sequences highly homologous to RING3. Primers were then prepared based on one of the EST sequences, and polymerase chain reaction was performed in a human testis cDNA library using the primers. As a result, a gene encoding a novel transcriptional regulator with a bromodomain was successfully isolated. By analyzing the expression of this gene, the inventors discovered that the gene is highly expressed in the testis cells. Moreover, the inventors found that a factor interacting with the transcriptional regulator, or a candidate pharmaceutical compound that regulates activity of the transcriptional regulator, can be screened by utilizing the transcriptional regulator and the gene encoding it.

Thus, the present invention relates to novel transcriptional regulators each having a bromodomain and the genes encoding them, and to a method of screening for a related factor or a candidate compound as a medicament using said proteins or genes, and more specifically relates to:

(1) a transcriptional regulator having a bromodomain, which comprises the amino acid sequence shown in SEQ ID NO:1, or said sequence wherein one or more amino acids are substituted, deleted, or added;

(2) a transcriptional regulator having a bromodomain, which is encoded by DNA hybridizing with DNA comprising the nucleotide sequence shown in SEQ ID NO:2;

(3) DNA coding for the transcriptional regulator according to (1) or (2);

(4) a vector comprising the DNA according to (3);

(5) a transformant expressibly retaining the DNA according to (3);

(6) a method for producing the transcriptional regulator according to (1) or (2), which comprises culturing the transformant according to (5);

(7) an antibody binding to the transcriptional regulator according to (1) or (2);

(8) a method of screening a compound having binding activity to the transcriptional regulator according to (1) or (2), wherein the method comprises
  (a) contacting a sample with the transcriptional regulator according to (1) or (2) and
  (b) selecting a compound having binding activity to the transcriptional regulator according to (1) or (2);

(9) a compound having binding activity to the transcriptional regulator according to (1) or (2), which can be isolated according to the method of (8);

(10) the compound according to (9), which is naturally occurring; and

(11) DNA specifically hybridizing with DNA comprising the nucleotide sequence shown in SEQ ID NO:2 and having at least 15 nucleotides.

Here, the term "transcriptional regulator(s)" means protein(s) that control gene expression, and "bromodomain" means an amino acid motif conserved among the transcriptional regulators associated with signal-dependent transcription, wherein said motif is involved in protein-protein interaction.

The present invention relates to a novel transcriptional regulator having a bromodomain. The amino acid sequence of the protein designated TSB contained in the transcriptional regulator of the present invention is shown in SEQ ID NO:1, and the nucleotide sequence of the cDNA encoding the protein is shown in SEQ ID NO:2. TSB protein is generally known as a region involved in interaction with other factors including transcriptional regulators, and it has a bromodomain(s) (amino acid positions 49–109 and 292–352 of SEQ ID NO:1), a characteristic motif of transcriptional regulators involved in cancer (FIG. 1). It is also highly expressed in the testis cells (Example 4). These facts suggest that TSB protein, like other transcriptional regulators having bromodomains, may be involved in cell proliferative diseases and cancers, particularly in testis cancer. In this connection, bromodomains are thought to play an important role. Thus, TSB protein, or a transcriptional regulator functionally equivalent thereto, can be used to prevent and treat cell proliferative diseases and cancers.

The transcriptional regulators of the present invention can be prepared as recombinant proteins generated using a recombinant gene technique, or as naturally-occurring proteins. The transcriptional regulators of the present invention include both recombinant and naturally-occurring proteins. The recombinant proteins can be prepared using a method such as incorporating DNA encoding a transcriptional regulator of the present invention as described below (e.g., DNA having the nucleotide sequence shown in SEQ ID NO:2) into a suitable expression vector, which is then introduced into host cells, and purifying the protein obtained from the transformant. The naturally occurring proteins can be prepared using a method such as preparing a column which utilizes an antibody obtained from a small animal immunized with the recombinant protein prepared as above or its partial peptide, and subjecting the extract from a tissue or cells in which a transcriptional regulator of the present invention is overexpressed (e.g., testis) to affinity chromatography using said column.

The present invention also relates to transcriptional regulators functionally equivalent to the transcriptional regulators of the present invention. A method of introducing mutation into amino acids of a protein to isolate such a protein is well known to one skilled in the art. Thus, it is well within the art of an ordinarily skilled person to isolate a protein functionally equivalent to the TSB protein having the amino acid sequence shown in SEQ ID NO:1 by appropriately modifying, for example, substituting amino acids without affecting the function of the protein using a site-directed mutagenesis system using PCR (GIBCO-BRL, Gaithersburg, Md.), a site-directed mutagenesis using oligonucleotides (Kramer, W. and Fritz, H. J. (1987), Methods in Enzymol., 154:350–367), or the similar methods. Mutation in an amino acid of a protein can also occur spontaneously. The transcriptional regulators of the present invention include those having the amino acid sequence (SEQ ID NO:1) of the TSB potein in which one or more amino acids are substituted, deleted, or added, and functionally equivalent to the TSB protein. The number of mutagenized amino acids is not particularly limited as long as it retains function equivalent to the TSB proiten. It is usually 50 amino acids or less, preferably 30 amino acids or less, more preferably 10 amino acids or less, and most preferably five amino acids or less.

As another method of isolating a functionally equivalent protein utilizing a hybridization technique (Sambrook, J. et al., Molecular Cloning 2nd ed. 9.47–9.58, Cold Spring Harbor Lab. press, 1989) is well known to one skilled in the art. Based on the DNA sequence encoding the TBS protein (SEQ ID NO:2), or the fragment thereof, a person with ordinary skill in the art can isolate DNA highly homologous to said DNA sequences using a hybridization technique (Sambrook, J. et al., Molecular Cloning 2nd ed. 9.47–9.58, Cold Spring Harbor Lab. press, 1989) to obtain a protein functionally equivalent to the TBS protein. The transcriptional regulators of the present invention include those encoded by DNA that hybridizes with DNA encoding the TBS protein and functionally equivalent to the TBS protein. Source organisms used to isolate a functionally equivalent protein includes, for example, mouse, rat, cattle, monkey, and pig as well as human. The hybridization and washing conditions for isolating DNA encoding a functionally equivalent protein are defined as low stringency: 42° C., 2×SSC, 0.1% SDS; moderate stringency: 50° C., 2×SSC, 0.1% SDS; and high stringency: 65° C., 2×SSC, 0.1% SDS. The higher the temperature, the more highly homologous DNA will be obtained. High amino acid homology means usually 40% or more, preferably 60% or more, more preferably 80% or more, or most preferably 95% or more. The transcriptional regulator obtained by the hybridization technique preferably contains bromodomain(s). It can also contain a serine/threonine kinase domain which functions to phosphorylate other proteins, PEST sequence which is a characteristic sequence of the proteins undergoing rapid intracellular proteolysis, and a nuclear transport signal which functions to tranport the protein into nucleus. The presence of the bromodomain in the protein can be identified by searching the bromodomain motif PROSITE database on DNASIS (HITACHI Software engineering).

The present invention also relates to DNA encoding a protein of the present invention. The DNA of the present invention includes cDNA, genomic DNA, and chemically synthesized DNA, but is not limited thereto as long as it codes for a protein of the present invention. cDNA can be prepared, for example, by designing a primer based on the nucleic acid sequence shown in SEQ ID NO:2 and performing plaque PCR (see Affara, N. A. et al. (1994), Genomics, 22:205–210). The genomic DNA can be prepared according to a standard technique using, for example, Qiagen genomic DNA kits (Qiagen, Hilden, Germany). The DNA sequence thus obtained can be determined according to a standard technique using a commercially available dye terminator sequencing kit (Applied Biosystems) and the like. In addition to applying to the production of recombinant proteins as described below, the DNA of the present invention may be applied to gene therapy and the like.

The present invention also relates to a vector into which the DNA of the present invention is inserted. The vector of the present invention includes various types of vectors, e.g. for expressing the protein of the present invention in vivo and for preparing recombinant proteins and appropriately selected depending on the purpose. Vectors used for expressing the protein of the present invention in vivo (in particular, for gene therapy) include the adenovirus vector pAdexLcw and the retrovirus vector pZIPneo. An expression vector is particularly useful for producing a protein of the present invention. Although there is no particular limitation to the expression vectors, the following vectors are preferred: pREP4 (Qiagen, Hilden, Germany) when $E.$ $coli$ is used; SP-Q01 (Stratagene, La Jolla, Calif.) when yeast is used; and BAC-to-BAC baculovirus expression system (GIBCO-BRL, Gaithersburg, Md.) when insect cells are used. A LacSwitch II expression system (Stratagene; La Jolla, Calif.) is advantageous when mammalian cells, such as CHO, COS, and NIH3T3 cells, are used. The DNA of the present invention can be inserted into vectors using a standard method.

The present invention also relates to a transformant expressibly retaining the DNA of the present invention. The transformants of the present invention include one harboring the above-described vector into which the DNA of the present invention is inserted and one having the DNA of the present invention integrated into its genome. The DNA of the present invention can be retained in the transformant in any form as long as the transformant expressibly retains the DNA of the present invention. There is no limitation to host. cells into which a vector of the present invention is introduced. If the cells are used to express a protein of the present invention for the purpose of ex vivo gene therapy, various cells can be used as target cells suited to diseases. Cells such as $E.$ $coli$, yeast cells, animal cells, and insect cells can be used for producing the protein of the present invention. The vector can be introduced into the cells by methods such as electroporation and the calcium phosphate method. Recombinant proteins can be isolated and purified from the transformants generated for producing the said proteins according to a standard method.

The present invention also relates to antibodies that bind to the transcriptional regulators of the present invention. The antibodies of the present invention include, but are not limited to, polyclonal and monoclonal antibodies. Also included are antisera obtained by immunizing an animal such as a rabbit with a protein of the present invention, any class of polyclonal or monoclonal antibodies, humanized antibodies generated by gene recombination, and human antibodies. The antibodies of the present invention can be prepared according to the following method. For polyclonal antibodies, antisera can be obtained by immunizing a small animal, such as a rabbit, with a transcriptional regulator of the present invention or a partial peptide thereof, then recovering the fractions that only recognize the transcriptional regulator of the present invention through an affinity column coupled with the transcriptional regulator of the present invention. Immunoglobulin G or M can be prepared by purifying the fractions through a Protein A or G column. For monoclonal antibodies, a small animal, such as a mouse, is immunized with a transcriptional regulator of the invention, the spleen is removed from the mouse and homogenized into cells, the cells are fused with myeloma cells from a mouse using a reagent such as polyethylene glycol, and clones that produce antibodies against the transcriptional regulator of the invention are selected from the resulting fused cells (hybridoma). The hybridoma obtained is then transplanted into the abdominal cavity of a mouse, and the ascites are recovered from the mouse. The obtained monoclonal antibodies can then be prepared by purifying, for example, by ammonium sulfate precipitation through a Protein A or G column, by DEAE ion exchanging chromatography, or through an affinity column coupled with the protein of the invention. Besides being used to purify or detect the transcriptional regulators of the present invention, the antiobodies of the present invention can beused as a drug for suppressing the functions of the transcriptional regulator of the present invention. When an antibody is used as a drug, a human or humanized antibody is effective with regard to immunogenicity. A human or humanized antibody can be prepared according to methods well known in the art. For example, a human antibody can be prepared by immunizing a mouse whose immune system is replaced by a human system with the transcriptional regulator of the present invention. A humanized antibody can be prepared by the CDR grafting method in which an antibody gene is cloned from monoclonal antibody-producing cells and its antigenic determinant site is transplanted to an existing human antibody.

The present invention also relates to a method for screening a compound that binds to transcriptional regulators of the present invention. The screening method of the present invention includes steps of (a) contacting a transcriptional regulator of the present invention with a test sample and (b) selecting a compound that has binding activity for the transcriptional regulator of the present invention. Test samples used for the screening include, but are not limited to, a library of synthetic low molecular weight compounds, a purified protein, an expression product of a gene library, a library of synthetic peptides a cell extract, and a supernatant of the cell culture. Various methods well known to one skilled in the art can be used for selecting a compound binding to a transcriptional regulator of the present invention.

A protein that-binds to a transcriptional regulator of the present invention can be screened by West-western blotting comprising steps of generating a cDNA library from the tissues of cells expected to express the protein that binds to a transcriptional regulator of the present invention (e.g., testis) using a phage vector ($\lambda$gt11, ZAPII, etc.), allowing the cDNA library to express on the LB-agarose plate, fixing the expressed proteins on a filter, reacting them with the transcriptional regulator of the present invention purified as a biotin-labeled protein or a fusion protein with GST protein, and detecting plaques expressing the protein bound to the regulator on the filter with streptavidin or anti-GST antibody (Skolnik, E. Y., Margolis, B., Mohammadi, M., Lowenstein, E., Fisher, R., Drepps, A., Ullrich, A. and Schlessinger, J. (1991), Cloning of PI3 kinase-associated p85 utilizing a novel method for expression/cloning of target proteins for receptor tyrosine kinases, Cell, 65:83–90). Alternatively, the method comprises expressing in yeast cells a transcriptional regulator of the present invention which is fused with SFR or GAL4 binding region, constructing a cDNA library in which proteins are expressed in a fusion protein with the transcription activation site of VP16 or GAL4 from the cells expected to express a protein that binds to the transcriptional regulator of the present invention, introducing the cDNA library into the above-described yeast cells, isolating the cDNA derived from the library from the detected positive clones, and introducing and expressing it in E. coli. (If a protein that binds to the transcriptional regulator of the present invention is expressed, a reporter gene is activated by the binding of the two proteins. The positive clones can then be identified.) This method can be performed using Two-hybrid system (MATCHMAKER Two-Hybrid System, Mammalian MATCHMAKER Two-Hybrid Assay Kit, MATCHMAKER One-Hybrid System (all from Clontech); HybriZAP Two-Hybrid Vector System (Stratagene) or in accordance with Dalton, S. and Treisman R. (1992), Characterization of SAP-1, a protein recruited by serum response factor to the c-fos serum response element, Cell, 68:597–612). Another method is to apply a culture supernatant or a cell extract from the cells suspected to express a protein which binds to the transcriptional regulator of the present invention onto an affinity column coupled with the transcriptional regulator of the present invention, and purify the protein specifically bound to the column.

Also well known to one skilled in the art are a method of screening molecules that bind to a transcriptional regulator of the present invention by reacting the immobilized transcriptional regulator of present invention with a synthetic compound, natural substance bank, or a random phage peptide display library, and a method of isolating low molecular weight compounds, proteins (or their genes), or peptides which bind to a transcriptional regulator of the present invention by utilizing the high-throughput technique of combinatorial chemistry (Wrighton, N. C., Farrell, F. X., Chang, R., Kashuyap, A. K., Barbone, F. P., Mulcahy, L. S., Johnson, D. L., Barrett, R. W., Jolliffe, L. K., Dower, W. J., Small peptides as potent mimetics of the protein hormone erythropoietin, Science (UNITED STATES) Jul. 26, 1996, 273:458–464; Verdine, G. L., The combinatorial chemistry of nature, Nature (ENGLAND), Nov. 7, 1996, 384:11–13; Hogan, J. C. Jr., Directed combinatorial chemistry, Nature (ENGLAND), Nov. 7, 1996, 384:17–19). The compounds thus isolated by the screening method of the present invention are candidates for drugs for enhancing or surpressing the activity of a transcriptional regulator of the present invention. When the compounds isolated by the screening method of the present invention are used as pharmaceuticals, they can be formulated by a known pharmacological process. For example, they can be administered to a patient with pharmaceutically acceptable carriers and vehicles (e.g., physiological saline, vegetable oil, a dispersant, a surfactant, and a stabilizer). The compounds may be percutaneously, intranasally, transbronchially, intramuscularly, intravenously, or orally administered, depending on their properties.

The present invention also relates to DNA specifically hybridizing with DNA coding the TBS protein and having at least 15 nucleotides. As used herein, "specifically hybridizing" means that no cross-hybridization occurs between DNA encoding other proteins under conditions of moderate stringency. Such DNA may be used as a probe for detecting and isolating the DNA encoding the TBS protein, and as a primer for amplifying the DNA encoding the protein of the present invention. Specific examples of the primers include those shown in SEQ ID NOs:3 and 4.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, and (iii) cell clones: e.g., as these occur in a DNA library such as a cDNA or genomic DNA library.

The term "substantially pure" as used herein in reference to a given polypeptide means that the polypeptide is substantially free from other biological compounds, such as those in cellular material,,viral material, or culture medium, with which the polypeptide was associated (e.g., in the course of production by recombinant DNA techniques or before purification from a natural biological source). The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "percent identity" of two amino acid sequences or of two nucleic acids is determined using the algorithm of Karlin and Altschul (*Proc. Natl. Acad. Sci. USA* 87:2264–2268, 1990), modified as in Karlin and Altschul (*Proc. Natl. Acad. Sci. USA* 90:4873–5877, 1993). Such an algorithm is incorporated into the NBLAST and XBLAST programs of Altschul et al. (*J. Mol Biol.* 215:403–410, 1990). BLAST nucleotide searches are performed with the NBLAST program, score=100, wordlength=12, to obtain nucleotide sequence homologous to a nucleic acid molecules of the invention. BLAST protein searches are performed with the XBLAST program, score=50, wordlength=3 to obtain amino acid sequences homologous to a reference polypeptide. To obtain gapped alignments for comparison purposes, Gapped BLAST is utilized as described in Altschul et al. (*Nucleic Acids Res.* 25;3389–3402, 19971). When utilizing BLAST and Gapped BLAST programs, the default parameters of the respective programs (e.g., XBLAST and NBLAST) are used. These programs can be found the World Wide Web at the web site of the National Center for Biotechnology Information NCBI).

Unless otherwise defined, all technical and scientific terms used herein have the same meaning as commonly understood by one of ordinary skill in the art to which this invention belongs. In case of conflict, the present application, including definitions, will control. All publications, patent applications, patents, and other references mentioned herein are incorporated by reference. The materials, methods, and examples are illustrative only and not intended to be limiting. Other features and advantages of the invention will be apparent from the detailed description, and from the claims.

BRIEF DESCRIPTION OF THE DRAWINGS

FIG. 1 shows the nucleic acid sequence (SEQ ID NO:2) of TSB aligned with the amino acid sequence (SEQ ID NO:1) of the open reading frame. The three motifs identified by the search of the PROSITE database are underlined. Two bromodomains (amino acid positions 49–109 and 292–352) and a PEST sequence (amino acid positions 636–672) are identified.

FIG. 2 compares the amino acid sequences of the predicted kinase domains of TSB (SEQ ID NOs:5–12), RING3 (SEQ ID NOs: 13–20), and fsh (SEQ ID NOs:21–28). The sub-domains of kinase are disclosed in Denis and Green, (1996) Genes and Devel. 10:261–271, and sub-domains I-II are excluded. The numerals correspond to the translation position of TSB. The conserved residues are shaded. adjacent markers on chromosome 1p determined by radiation hybrid analysis.

FIG. 4A shows the results of Northern blot analysis of TSB in the normal tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, ovary; Lane 14, small intestine; Lane 15, colon (mucous lining); and Lane 16, peripheral leukocytes).

FIG. 4B shows the results of Northern blot analysis of TSB in carcinoma cell lines (Lane 1, promyelocytic leukemia HL-60; Lane 2, HeLa S3 cells; Lane 3, chronic myelocytic leukemia K-56; Lane 4, lymphoblastic leukemia MOLT-4; Lane 5, Burkitt's lymphoma Raji; Lane 6, large intestinal adenocarcinoma SW480; Lane 7, lung carcinoma S549; and Lane 8, melanoma G361). The positions of molecular weight markers are indicated on the right.

BEST MODE FOR IMPLEMENTING THE INVENTION

Figure 3:
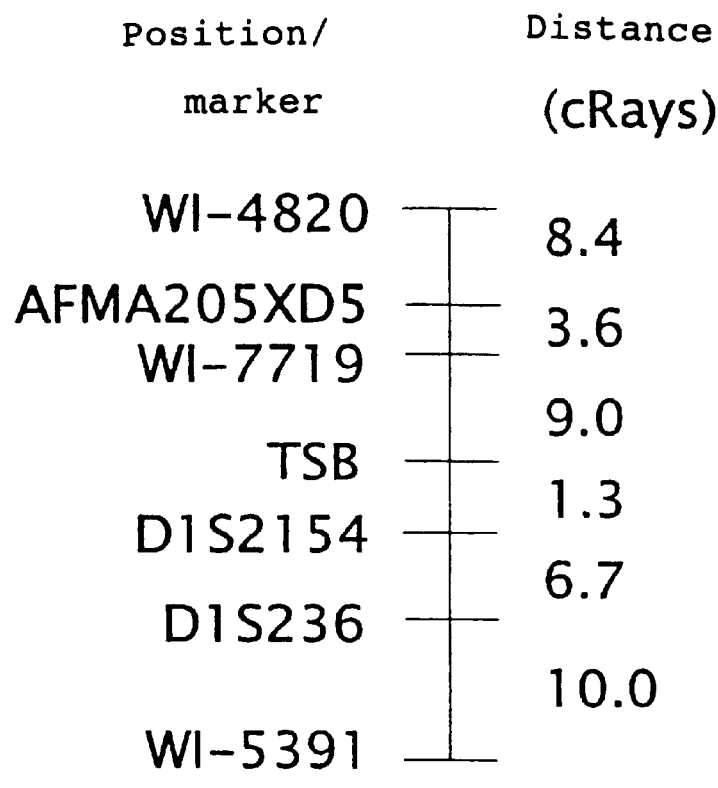
FIG. 3 shows the map location of TSB. The position is indicated relative to the positions of the adjacent markers on the chromosome 1p determined by radiation hybrid analysis.

The following examples illustrate the present invention in more detail, but are not to be construed to limit the scope of the present invention.

EXAMPLE 1

Identification of EST Homologous to RING3 and Isolation of its Full-length Sequence A BLAST search of the EST database identified numerous ESTs homologous to the DNA sequence of the RING3 gene (Beck et al., (1992), DNA Seq. 2:203–210) used as a probe. Among these ESTs, EST H64204, which was derived from a testis- specific cDNA library (Diatchenko et al., (1996) Proc. Natl. Acad. Sci. USA 93:6025–6030), had 65% sequence homology to RING3 spanning 285 bp.

To clone the full-length sequence of EST H64204, PCR primers U (AATGTCTCTGCCAAGTCGACAA; SEQ ID NO:3) and L (AGCATCCACAGGACGTTGAAAG; SEQ ID NO:4) were designed to perform PCR using testis cDNAs as templates. PCR was carried out at 94° C. for 8 min. followed by 35 cycles of 94° C. for 30 sec (heat annealing), 60° C. for 1 min (annealing), and 72° C. for 1 min (extension). AmpliTaq gold (Perkin Elmer) was used as an enzyme for PCR. This resulted in a PCR product of 175 bp. Subsequently, a testis cDNA library was screened (Clontech; HL3024a) using this PCR product as a probe. All the probes were labeled with [$-^{32}$P]dCTP by random priming and were purified through Chromaspin (10 columns; Clontech). Hybridization was performed in ExpressHyb hybridization solution (Clontech) for 1 hour at 65°. The filter was washed at the final stringency of 1×SSC, 0.1% SDS, 65° C. The sequence of a cDNA clone that was aligned with the EST sequence was used to re-screen the library. This process was repeated until a series of overlapped clones giving a full-length sequence of the coding region of the gene was obtained. As a result, a continuous sequence of 3,104 bp encoding 947 amino acids was found in an open reading frame (ORF) at the nucleotide positions 106–2946. The ORF is followed by a short stretch of a 3' untranslated region of 60 bp, which is terminated with a poly(A) tail that has a polyadenylated signal (ATTAAA) in the 20 bp upstream of it. The inventors designated the isolated clone "TSB (testis specific bromodomain). SEQ ID NO:2 shows the nucleotide sequence of TSB along with the predicted amino acid sequence thereof. The predicted amino acid sequence is also shown in SEQ ID NO:1. The nucleotide sequences were determined with the automated sequencer ABI377 (Perkin Elmer) by use of ABI dye terminator chemistry.

EXAMPLE 2

Homology and Motifs

RING3 (66% homology, 59% identity spanning 649 amino acids), D26362 (62% homology, 56% identity spanning 649 amino acids), and fsh (62% homology, 56% identity spanning 565 amino acids) were identified as the amino acid sequences having the highest homology with TBS by searching protein databases.

Figure 1:
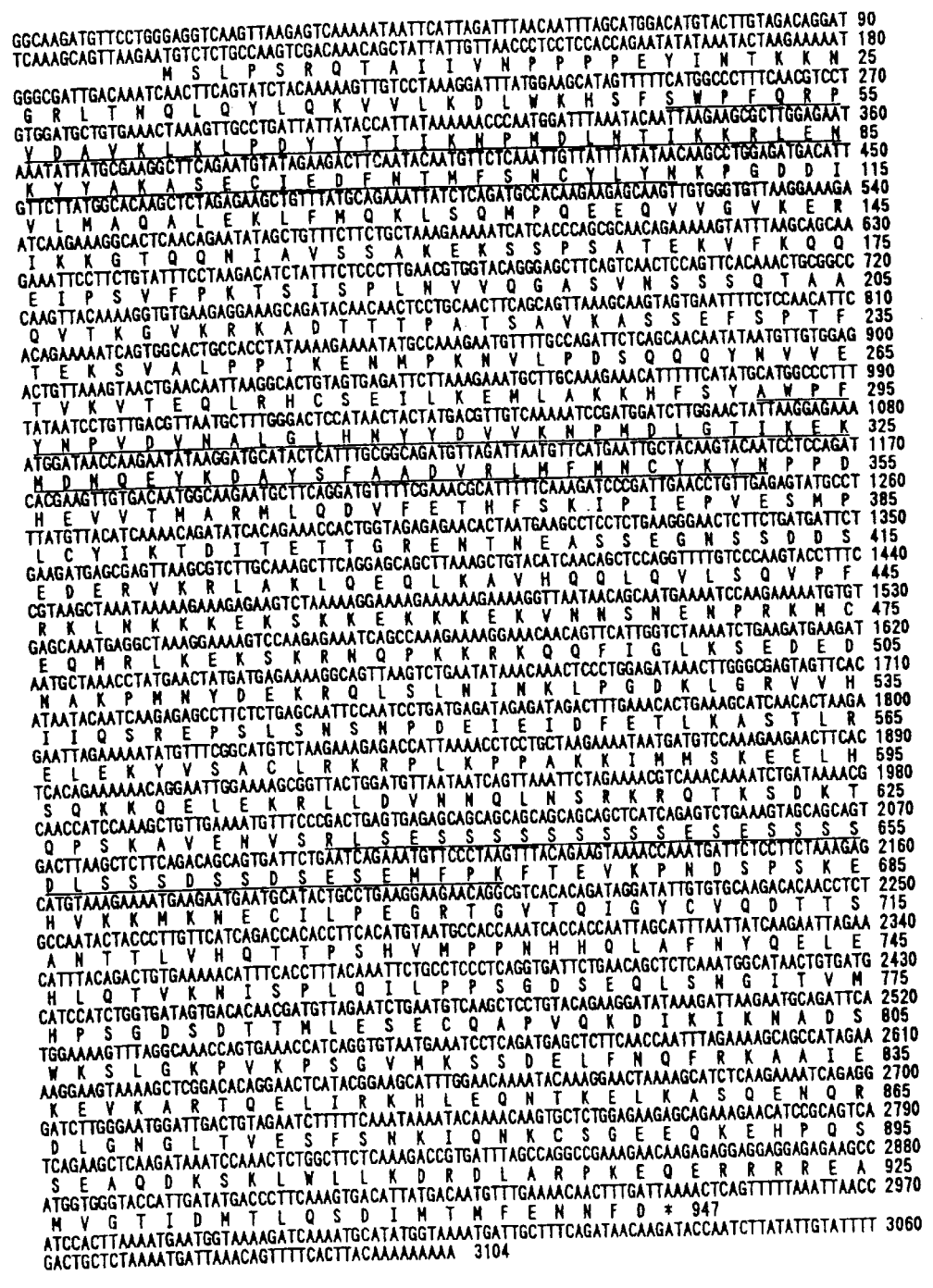

Two bromodomains (amino acid positions 49–109 and 292–352) were identified by searching the PROSITE database for the motif of amino acid sequence. A PEST sequence (Rodgers et al., (1986) Science 234:364) was also present in amino acid positions 636–672. FIG. 1 shows the locations of these motifs.

Since RING3 is also known to have serine-threonine kinase activity (Denis and Green, (1996) Genes and Devel. 10:261–271), the amino acid sequence of TSB was compared with that of the predicted kinase domain of RING3 using Bestfit at GCG. The result showed that the predicted kinase domain of RING3 is very well conserved in TSB (FIG. 2). However, it was found that TBS did not contain sub-domain I, which codes for the predicted ATP-binding domain, and sub-domain II, which codes for catalytic lysine, suggesting that the kinase activity of TSB was possibly lost.

In addition, since the RING3 protein is known to be localized in the nucleus, the predicted nuclear transport signal of TSB was identified using the PSORT program. As a result, four copies of the nuclear transport signal (in the 488, 489, 575 and 919 positions), each copy consisting of four residues, and two copies of Robins and Dingwall consensus sequence (Robins and Dingwall, (1991) Cell 64:615–23) (in the 445 and 603 positions) were discovered. Thus, like RING3, nuclear localization of TSB was also indicated.

EXAMPLE 3

Mapping of TSB

To identify the locus of TSB, DNA from 24 human/rodent single chromosomal somatic cell lines obtained from Coriell Cell Repositories, New Jersey (Dubois and Naylor, (1993) Genomics 16:315–319) were amplified using primers U (SEQ ID NO:3) and L (SEQ ID NO:4).

A panel of single chromosomal hybrid cell lines was screened for the TSB-localized region, using primers U (SEQ ID NO:3) and L (SEQ ID NO:4). As a result, the predicted product of 175 bp was amplified only in the cell line GM 13139, a single chromosomal cell line for human chromosome 1. The same primers were used for PCR for a GeneBridge4 radiation hybrid panel (Walter et al., (1994) Nature Genetics 7:22–28). The binary codes generated by assessing each hybrid as positive or negative for the amplification were compared with the analogous codes for the markers constituting the framework map, using the server located on the World Wide Web at the web site of the Whitehead Institute for Biomedical Research/MIT Center for Genome Research. This procedure was repeated to give independent scores. The two experiments yielded identical binary codes, and TSB was shown to be located on chromosome 1p between markers WI-7719 and WI-3099 (D1S2154) (FIG. 3).

EXAMPLE 4

Analysis of TSB Expression

Northern analysis of 16 normal tissues was conducted using the probe prepared by PCR amplification of the testis cDNAs using primers U (SEQ ID NO:3) and L (SEQ ID NO:4). The probe strongly hybridized with mRNA of 3.5 kb and weakly hybridized with that of 4.0 kb (FIG. 4A). This result was consistent with the source testis-specific library of the EST used to identify TSB (Diatchenko et al., (1996) Proc. Natl. Acad. Sci. USA 93:6025–6030). In addition, the probe cross-hybridized with the two species of mRNA (about 2.0 and 4.5 kb) commonly expressed in these tissues. Since this probe contained the sequence encoding a bromodomain, the transcripts of the two species potentially represent other bromodomain genes. Furthermore, a panel of mRNA derived from eight tumor cell lines was screened along with the panel of the normal tissues, since, several other testis-specific genes, in particular the MAGE family (van der Bruggen et al., (1991) Science 254:1643–1647) are expressed in tumor tissues. However, expression of TSB was not detected in any of the cell lines tested (FIG. 4B). Likewise, a panel of 10 samples of lung cancer was negative for the TSB expression (data are not shown). The conditions for hybridization were the same as those described in Example 1.

INDUSTRIAL APPLICABILITY

The present invention provides a novel transcriptional regulator having a bromodomain, DNA encoding said transcriptional regulator, a vector carrying said DNA, a transformant expressibly retaining said DNA, an antibody binding to said transcriptional regulator, and a method of screening a compound that binds to said transcriptional regulator. The transcriptional regulator of the present invention is considered to form a family together with a transcriptional regulator RING3 that is thought to be associated with cancer. It is abundantly expressed in the testis. Accordingly, the transcriptional regulator of the present invention and DNA encoding said transcriptional regulator can be used to screen for therapeutics to treat diseases such as cell-proliferative diseases and cancer, particularly testis cancer; diseases attributed to aplasia and dysfunction of sperm; or for contraceptives. Antibodies and other compounds that bind to the transcriptional regulator of the present invention can also be used as therapeutics.

What is claimed is:

1. A substantially pure polypeptide comprising an amino acid sequence having at least 60% identity to SEQ ID NO: 1, wherein the polypeptide regulates transcription of a gene and comprises a bromodomain, but lacks an ATP-binding domain.

2. The polypeptide of claim 1, wherein the amino acid sequence has at least 70% identity to SEQ ID NO:1.

3. The polypeptide of claim 1, wherein the amino acid sequence has at least 80% identity to SEQ ID NO: 1.

4. The polypeptide of claim 1, wherein the amino acid sequence has at least 90% identity to SEQ ID NO: 1.

5. A substantially pure polypeptide comprising SEQ ID NO:1.

6. A substantially pure polypeptide comprising the amino acid sequence of SEQ ID NO:1, with up to 30 conservative amino acid substitutions, wherein the polypeptide regulates transcription of a gene and comprises a bromodomain, but lacks an ATP-binding domain.

7. A substantially pure polypeptide encoded by a nucleic acid that hybridizes under highly stringent conditions to a probe consisting of SEQ ID NO:2, wherein the polypeptide regulates transcription of a gene and comprises a bromodomain, buts lacks an ATP-binding domain.

8. A substantially pure polypeptide consisting of SEQ ID NO:1.

9. A substantially pure polypeptide comprising an amino acid sequence having at least 60% identity to SEQ ID NO:1, wherein the polypeptide regulates transcription of a gene, comprises a bromodomain, and does not bind ATP.

10. The polypeptide of claim 9, wherein the amino acid sequence has at least 70% identity to SEQ ID NO:1.

11. The polypeptide of claim 9, wherein the amino acid sequence has at least 80% identity to SEQ ID NO:1.

12. The polypeptide of claim 9, wherein the amino acid sequence has at least 90% identity to SEQ ID NO:1.

13. A substantially pure polypeptide comprising the amino acid sequence of SEQ ID NO:1, with up to 30 conservative amino acid substitutions, wherein the polypeptide regulates transcription of a gene, comprises a bromodomain, and does not bind ATP.

14. A substantially pure polypeptide encoded by a nucleic acid that hybridizes under highly stringent conditions to a probe consisting of SEQ ID NO:2, wherein the polypeptide regulates transcription of a gene, comprises a bromodomain, and does not bind ATP.

15. A substantially pure polypeptide comprising an amino acid sequence having at least 60% identity to SEQ ID NO:1, wherein the polypeptide regulates transcription of a gene and comprises a bromodomain, but lacks a catalytic lysine.

16. The polypeptide of claim 15, wherein the amino acid sequence has at least 70% identity to SEQ ID NO:1.

17. The polypeptide of claim 15, wherein the amino acid sequence has at least 80% identity to SEQ ID NO:1.

18. The polypeptide of claim 15, wherein the amino acid sequence has at least 90% identity to SEQ ID NO:1.

19. A substantially pure polypeptide comprising the amino acid sequence of SEQ ID NO:1, with up to 30 conservative amino acid substitutions, wherein the polypeptide regulates transcription of a gene and comprises a bromodomain, but lacks a catalytic lysine.

20. A substantially pure polypeptide encoded by a nucleic acid that hybridizes under highly stringent conditions to a probe consisting of SEQ ID NO:2, wherein the polypeptide regulates transcription of a gene and comprises a bromodomain, but lacks a catalytic lysine.

21. A substantially pure polypeptide comprising an amino acid sequence having at least 60% identity to SEQ ID NO:1, wherein the polypeptide regulates transcription of a gene and comprises a bromodomain, but lacks kinase activity.

22. The polypeptide of claim 21, wherein the amino acid sequence has at least 70% identity to SEQ ID NO:1.

23. The polypeptide of claim 21, wherein the amino acid sequence has at least 80% identity to SEQ ID NO:1.

24. The polypeptide of claim 21, wherein the amino acid sequence has at least 90% identity to SEQ ID NO:1.

25. A substantially pure polypeptide comprising the amino acid sequence of SEQ ID NO:1, with up to 30 conservative amino acid substitutions, wherein the polypeptide regulates transcription of a gene and comprises a bromodomain, but lacks kinase activity.

26. A substantially pure polypeptide encoded by a nucleic acid that hybridizes under highly stringent conditions to a probe consisting of SEQ ID NO:2, wherein the polypeptide regulates transcription of a gene and comprises a bromodomain, but lacks kinase activity.

27. A method of screening for a compound that binds to a polypeptide, the method comprising providing a polypeptide comprising an amino acid sequence, having at least 60% identity to SEQ ID NO:1, wherein the polypeptide regulates gene transcription and comprises a bromodomain, but lacks an ATP-binding domain;

contacting a test compound with the polypeptide;
determining whether the test compound has bound to the polypeptide, and
selecting a compound that binds to the polypeptide.

28. A method of screening for a compound that binds to a polypeptide, the method comprising:
providing the polypeptide of claim 2;
contacting a test compound with the polypeptide;
determining whether the test compound has bound to the polypeptide, and
selecting a compound that binds to the polypeptide.

29. A method of screening for a compound that binds to a polypeptide, the method comprising:
providing the polypeptide of claim 3;
contacting a test compound with the polypeptide;
determining whether the test compound has bound to the polypeptide, and
selecting a compound that binds to the polypeptide.

30. A method of screening for a compound that binds to a polypeptide, the method comprising:
providing the polypeptide of claim 4;
contacting a test compound with the polypeptide;
determining whether the test compound has bound to the polypeptide, and
selecting a compound that binds to the polypeptide.

31. A method of screening for a compound that binds to a polypeptide, the method comprising:
providing the polypeptide of claim 5;
contacting a test compound with the polypeptide;
determining whether the test compound has bound to the polypeptide, and
selecting a compound that binds to the polypeptide.

32. A method of screening for a compound that binds to a polypeptide, the method comprising:
providing the polypeptide of claim 6;
contacting a test compound with the polypeptide;
determining whether the test compound has bound to the polypeptide, and
selecting a compound that binds to the polypeptide.

33. A method of screening for a compound that binds to a polypeptide, the method comprising:
providing the polypeptide of claim 7;
contacting a test compound with the polypeptide;
determining whether the test compound has bound to the polypeptide, and
selecting a compound that binds to the polypeptide.

34. A method of screening for a compound that binds to a polypeptide, the method comprising:
providing the polypeptide of claim 9;
contacting a test compound with the polypeptide;
determining whether the test compound has bound to the polypeptide, and
selecting a compound that binds to the polypeptide.

35. A method of screening for a compound that binds to a polypeptide, the method comprising:
providing the polypeptide of claim 10;
contacting a test compound with the polypeptide;
determining whether the test compound has bound to the polypeptide, and
selecting a compound that binds to the polypeptide.

36. A method of screening for a compound that binds to a polypeptide, the method comprising:
providing the polypeptide of claim 11;
contacting a test compound with the polypeptide;
determining whether the test compound has bound to the polypeptide, and
selecting a compound that binds to the polypeptide.

37. A method of screening for a compound that binds to a polypeptide, the method comprising:
providing the polypeptide of claim 12;
contacting a test compound with the polypeptide;
determining whether the test compound has bound to the polypeptide, and
selecting a compound that binds to the polypeptide.

38. A method of screening for a compound that binds to a polypeptide, the method comprising:
providing the polypeptide of claim 13;
contacting a test compound with the polypeptide;
determining whether the test compound has bound to the polypeptide, and
selecting a compound that binds to the polypeptide.

39. A method of screening for a compound that binds to a polypeptide, the method comprising:
providing the polypeptide of claim 14;
contacting a test compound with the polypeptide;
determining whether the test compound has bound to the polypeptide, and
selecting a compound that binds to the polypeptide.

40. A method of screening for a compound that binds to a polypeptide, the method comprising:
providing the polypeptide of claim 15;
contacting a test compound with the polypeptide;
determining whether the test compound has bound to the polypeptide, and
selecting a compound that binds to the polypeptide.

41. A method of screening for a compound that binds to a polypeptide, the method comprising:
providing the polypeptide of claim 16;
contacting a test compound with the polypeptide;
determining whether the test compound has bound to the polypeptide, and
selecting a compound that binds to the polypeptide.

42. A method of screening for a compound that binds to a polypeptide, the method comprising:
providing the polypeptide of claim 17,
contacting a test compound with the polypeptide;
determining whether the test compound has bound to the polypeptide, and
selecting a compound that binds to the polypeptide.

43. A method of screening for a compound that binds to a polypeptide, the method comprising:
providing the polypeptide of claim 18;
contacting a test compound with the polypeptide;
determining whether the test compound has bound to the polypeptide, and
selecting a compound that binds to the polypeptide.

44. A method of screening for a compound that binds to a polypeptide, the method comprising:
providing the polypeptide of claim 19;
contacting a test compound with the polypeptide;
determining whether the test compound has bound to the polypeptide, and
selecting a compound that binds to the polypeptide.

45. A method of screening for a compound that binds to a polypeptide, the method comprising:
provide the polypeptide of claim 20;
contacting a test compound with the polypeptide;
determining whether the test compound has bound to the polypeptide, and
selecting a compound that binds to the polypeptide.

46. A method of screening for a compound that binds to a polypeptide, the method comprising:
providing the polypeptide of claim 21;
contacting a test compound with the polypeptide;
determining whether the test compound has bound to the polypeptide, and
selecting a compound that binds to the polypeptide.

47. A method of screening for a compound that binds to a polypeptide, the method comprising:
providing the polypeptide of claim 22;
contacting a test compound with the polypeptide;
determining whether the test compound has bound to the polypeptide, and
selecting a compound that binds to the polypeptide.

48. A method of screening for a compound that binds to a polypeptide, the method comprising:
providing the polypeptide of claim 23;
contacting a test compound with the polypeptide;
determining whether the test compound has bound to the polypeptide, and
selecting a compound that binds to the polypeptide.

49. A method of screening for a compound that binds to a polypeptide, the method comprising:
providing the polypeptide of claim 24;
contacting a test compound with the polypeptide;
determining whether the test compound has bound to the polypeptide, and
selecting a compound that binds to the polypeptide.

50. A method of screening for a compound that binds to a polypeptide, the method comprising:
providing the polypeptide of claim 25;
contacting a test compound with the polypeptide;
determining whether the test compound has bound to the polypeptide, and
selecting a compound that binds to the polypeptide.

51. A method of screening for a compound that binds to a polypeptide, the method comprising:
providing the polypeptide of claim 26;
contacting a test compound with the polypeptide;
determining whether the test compound has bound to the polypeptide, and
selecting a compound that binds to the polypeptide.

* * * * *

UNITED STATES PATENT AND TRADEMARK OFFICE
CERTIFICATE OF CORRECTION

PATENT NO. : 6,504,009 B1
DATED : January 7, 2003
INVENTOR(S) : Michael H. Jones It is certified that error appears in the above-identified patent and that said Letters Patent is hereby corrected as shown below:

Title Page,
Item [56], References Cited, OTHER PUBLICATIONS, "Beck et al.," reference, replace "*Drosphila*" with -- *Drosophila* --; "Haynes et al." and "Jones et al.," references, replace "*Drosphila*" with -- *Drosophila* --; and replace "Bromodoma in" with -- Bromodomain --.

Column 1,
Line 24, after "USA," delete "25".

Column 4,
Line 51, after "TSB" replace "proiten" with -- protein --.

Column 6,
Line 48, replace "antiobodies" with -- antibodies --;
Line 48, replace "beused" with -- be used --.

Column 7,
Line 10, delete "-" between "that" and "binds".

Column 8,
Line 52, after "material" delete second comma.

Column 9,
Line 11, replace "4873" with -- 5873 --.
Line 22, replace "19971" with -- 1997 --.
Lines 54-56, after "shaded." delete "adjacent markers.......analysis."
Line 60, before "chromosome" delete "the".

Column 10,
Line 39, "[-$^{32}$P]" should be --[$\alpha$-$^{32}$P] --.
Line 42, "65°" should be -- 65° C --.

UNITED STATES PATENT AND TRADEMARK OFFICE
CERTIFICATE OF CORRECTION

PATENT NO. : 6,504, 009 B1
DATED : January 7, 2003
INVENTOR(S) : Michael H. Jones It is certified that error appears in the above-identified patent and that said Letters Patent is hereby corrected as shown below:

Column 32
Line 62, after "comprising" should be -- comprising: --.
Line 64, after "sequence" delete the comma.

Signed and Sealed this

First Day of June, 2004

JON W. DUDAS
*Acting Director of the United States Patent and Trademark Office*